United States Patent [19]
Bove

[11] Patent Number: 6,065,210
[45] Date of Patent: May 23, 2000

[54] MAGNETOTHERAPEUTIC BACK MASSAGER AND METHOD OF MAKING SAME

[75] Inventor: Thomas A. Bove, Spokane, Wash.

[73] Assignee: Nu-Magnetics, Inc., Port Jefferson, N.Y.

[21] Appl. No.: 09/088,917

[22] Filed: Jun. 2, 1998

[51] Int. Cl.⁷ .................................................. B23P 15/00
[52] U.S. Cl. .................................. 29/895.21; 29/895.31; 492/8; 601/19
[58] Field of Search ........................... 29/895.21, 895.31; 492/8, 13; 601/118, 119, 120, 123, 19; 600/9

[56] References Cited

U.S. PATENT DOCUMENTS

| | | |
|---|---|---|
| 444,597 | 1/1891 | Lichtenstadt et al. . |
| 1,239,539 | 9/1917 | Swenson . |
| 4,640,808 | 2/1987 | Okumura et al. ............................ 492/8 |
| 4,691,693 | 9/1987 | Sato .......................................... 128/24 |
| 4,727,857 | 3/1988 | Horl .......................................... 128/1.3 |
| 4,744,350 | 5/1988 | Sato .......................................... 128/57 |
| 5,143,056 | 9/1992 | Ih-Jong ...................................... 128/57 |
| 5,158,526 | 10/1992 | Bricot ......................................... 600/9 |
| 5,226,185 | 7/1993 | Guay et al. ................................. 5/448 |
| 5,233,768 | 8/1993 | Humphreys ................................ 36/44 |
| 5,277,692 | 1/1994 | Ardizzone .................................. 600/9 |
| 5,304,111 | 4/1994 | Mitsuno et al. ............................ 600/9 |
| 5,382,222 | 1/1995 | Yih-Jong .................................. 601/135 |
| 5,488,755 | 2/1996 | Chang ....................................... 16/111 |
| 5,575,760 | 11/1996 | Masuda ..................................... 601/19 |
| 5,621,969 | 4/1997 | Masuda .................................. 29/895.21 |
| 5,649,362 | 7/1997 | Yamamoto et al. .................. 29/895.21 |

*Primary Examiner*—I Cuda
*Attorney, Agent, or Firm*—Cislo & Thomas LLP

[57] ABSTRACT

A method for manufacturing a magnetotherapeutic back massager. A roller blank having a central cylindrical core circumscribed by a pair of spaced apart circular projections receives magnets in the circular projections to provide magnetic properties to the resultingly constructed magnetotherapeutic back massager. Preferably, the magnets are arranged so as to alternate polarity and a magnet-supporting strip holds the magnets together prior to and during the association of the magnets with the circular projections. The circular projections may have indentations or grooves to accommodate the magnets. Once the magnets have been associated with the circular projections, the magnets are more permanently attached by applying additional material to the circular projections so as to seal the magnets to the circular projections. The sealing material may be the same as that used to construct the roller blank, preferably latex rubber. Either prior to or after the sealing process, the magnet-supporting strip is removed from the magnets leaving them held in place by the circular projections of the roller blank. A cover, preferably bi-lobed and knobbed, is then applied to the now-magnetized roller blank. Roller bearings attached to the roller blank allow the central, bi-lobed massaging core to articulate rotatably with respect to the central spindle shaft. The central spindle shaft may have handles at opposite ends to facilitate manipulation of the resultingly-constructed magnetotherapeutic back massager.

22 Claims, 3 Drawing Sheets

MAGNETOTHERAPEUTIC BACK MASSAGER AND METHOD OF MAKING SAME

BACKGROUND OF THE INVENTION

1. Field of the Invention

This invention relates to back massagers that roll upon a spindle shaft, and more particularly to a method of making a magnetotherapeutic back massager that uses magnets to invoke magnetotherapeutic response in the person being massaged.

2. Description of the Related Art

Magnetotherapy uses magnetic fields to provide therapeutic and restorative treatment to limbs, organs, and other parts of the body. Generally, one means by which magnetotherapy may be achieved is by bringing a magnet or series of magnets into close proximity with the affected body part or organ of interest. As is known according to Faraday's Law of Magnetic Induction, as well as the Hall Effect, charged particles experience a force acting on them when they move through a magnetic field in a perpendicular direction. Since human blood is replete with ions and electrolytes, it has many charged particles which experience a force, including an aligning force, when moving through a magnetic field. When exposed and caused to so travel through a magnetic field, such ions and electrolytes may generate heat, causing the associated blood vessel to widen. The widening of the blood vessel would then allow increased volumes of blood to flow through the blood vessel.

Additional therapeutic or restorative effects might arise through the alignment of polar molecules as they pass through the magnetic field. When passing through a magnetic field, polar molecules rotate to align themselves with the field. Such alignment would alternate with the magnetic polarity as the polar molecules traveled through different regions of such magnetic polarity. The mechanical motion of the rotation of such polar molecules might also cause heating and the like and would also stimulate, mix, or agitate the blood in a gentle manner, causing it to gently churn. Such mixing of the blood at the molecular level may cause it to more easily recognize foreign matter. By recognizing foreign matter, the blood and/or immune system may be able to more readily address such foreign matter.

Several patents are known having various designs for the alternation of magnets of different polarity to provide spatially diverse magnetic fields. The patent to Latzke (U.S. Pat. No. 4,489,711 issued Dec. 25, 1984) and the patents to Ardizzone (U.S. Pat. No. 5,277,692 issued Jan. 11, 1994; U.S. Pat. No. 5,514,072 issued May 7, 1996; and U.S. Pat. No. 5,538,495 issued Jul. 23, 1996) all disclose a variety of magnetic plaster and magnetic pads having certain magnetic geometries in order to achieve spatially varying magnetic fields through the use of magnets.

Magnetotherapy can also be applied through a variety of other agents and devices. Particularly, massage is known in the Orient and is increasingly becoming common in the Occident with respect to use as a therapeutic device. By massaging the muscles and articulating the limbs, better flow of body fluids such as blood and lymph can occur and the masseur or masseuse can detect and address certain muscular or anatomical features which have occurred as a result of stress, strain, or from some other cause. For example, muscle knots and the like can be massaged out by the massager. Additionally, in articulating the joints, the massager may become more aware of certain limitations in articulation that can be addressed through physical massage therapy or the like.

Of particular importance with respect to massage is the back, or spine, about which the remaining skeletal frame is hung by means of muscles, tendons, ligaments, and the like. While devices facilitating back massage are known in the art, only a very few of these combine magnetotherapy with back massage. Of these, the patent to Masuda (U.S. Pat. No. 5,575,760 issued Nov. 19, 1996) shows a earlier therapeutic appliance meant for use in back massage. The device in the Masuda patent shows generally a knobbed, bi-lobed back massager having a pair of oppositely opposed handles about a central and freely rotating back massager portion. In a generally back-and-forth motion over the person's back, the knobbed, bi-lobed portion is pressed against the person's back so that the lobes are straddled the person's spine. By rolling the Masuda device over the person's back, massage of the back is thereby attained and greater relaxation and muscular engagement by the massager is accomplished.

As set forth in the Masuda patent, an aluminum wheel or the like is used to support the magnets providing the magnetotherapeutic effect arising therein. Additionally, and as shown in FIG. 8 of the Masuda patent, the central core rolling structure of the Masuda device is accomplished in a series of manufacturing steps that require some, awkward manipulation of the magnets and may not use materials that are most advantageous for realizing magnetotherapy through a back-massaging device.

In order to further the art, and to provide better means by which magnetotherapeutic back massagers of the Masuda type may be achieved, it would be more advantageous to provide a means of manufacturing a magnetotherapeutic back massager that is more easily realized and more conveniently realized by current manufacturing techniques.

SUMMARY OF THE INVENTION

The present invention resides in a method by which magnetothereutic back massagers may be fabricated. In realizing the present invention, certain economies and efficiencies are realized that enable the more optimal manufacturing, making, and construction of magnetotherapeutic back massagers. Generally, such back massagers have dual lobes that straddle the spine during the massaging process.

A roller blank, preferably made of latex rubber, is first made in anticipation of the addition of magnets for magnetotherapeutic use. The roller blank generally has a hollow cylindrical core about which circulation projections are disposed perpendicular to the main axis of the hollow cylindrical core. These cylindrical projections serve as housings for the magnets used in the magnetotherapeutic back massager.

Once the latex roller blank cord has been made, magnets are arranged on a magnet-supporting strip so that the magnets may be pre-arranged for incorporation into the roller blank. Preferably, the magnets are arranged so that they alternate in polarity. After so arranging the magnets on the magnetic strip, the magnets are then attached to one of the circular projections of the roller blank. As the magnet-supporting strip is preferably approximately one-half the circumference of the associated circular projection, an entire circular projection can be set with magnets by using two magnet-supporting strips with magnets. Once the magnets are set to the circular projections, the magnets may be more permanently attached to the circular projections by adding additional latex material and the magnet-supporting structure removed, or vice versa, as these two steps are generally interchangeable so long as the magnets are appropriately attached to the circular projections.

Once the magnets have been attached to the circular projections are the magnet-supporting strip has been removed, the magnetic roller core of the magnetotherapeutic back massager is then ready to be covered with a cosmetically attractive, therapeutically knobbed, or other preferred covering. Additionally, roller bearings or the like can be used at both ends of the magnetized roller blank in order to receive the spindle shaft. The roller bearings allow the magnetized core to rotate with respect to the spindle shaft. The spindle shaft may have handles at both ends to make engagement of the constructed magnetotherapeutic back massager easier.

OBJECTS OF THE INVENTION

It is an object of the present invention to provide a method by which a magnetotherapeutic back massager can be more easily constructed.

It is another object of the present invention to provide such a method that allows the easy application and association of the magnetotherapeutic magnets with the roller core of the magnetotherapeutic back massager.

It is an additional object of the present invention to provide a magnetotherapeutic back massager that does not inhibit the magnetic effect of incorporated magnets.

These and other objects and advantages of the present invention will be apparent from a review of the following specification and accompanying drawings.

DESCRIPTION OF THE PREFERRED EMBODIMENT(S)

Figure 1:
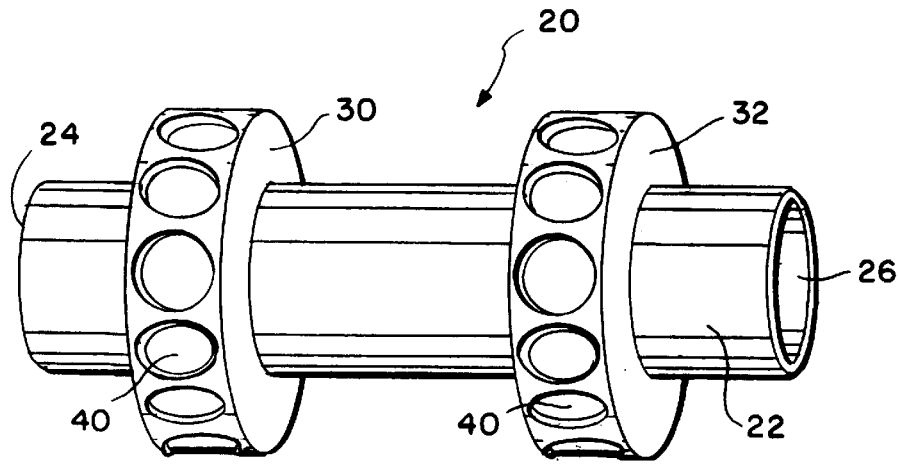
FIG. 1 is a preferred embodiment of the roller blank core of the magnetotherapeutic back massager of the present inventive method.
Figure 2:
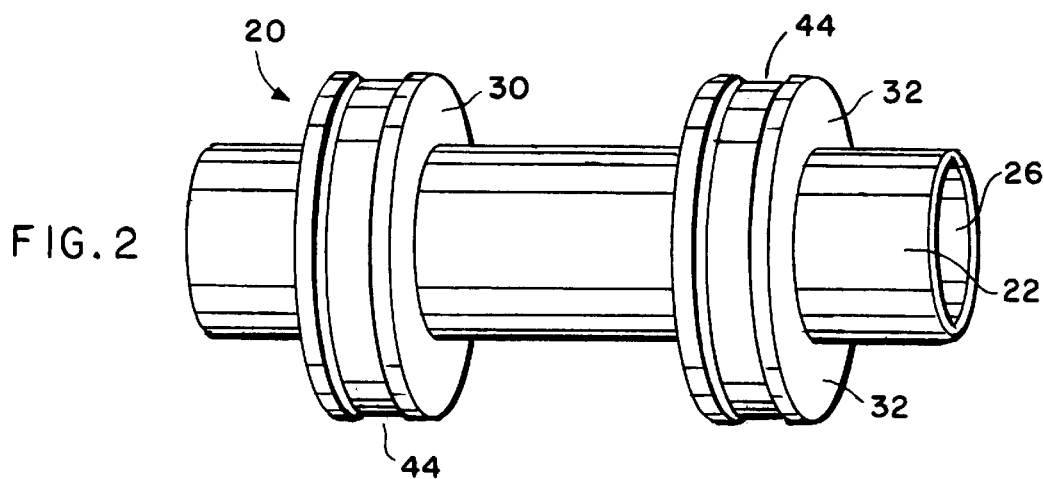
FIG. 2 is a front perspective view of an alternative roller blank core for the magnetotherapeutic back massager for use in the present inventive method.

The present invention resides in a novel method by which a magnetotherapeutic back massager may be more efficiently and conveniently formed, constructed, and manufactured. By making the manufacturing process easier, more economical use of resources and more efficient manufacturing techniques can be implemented. Additionally, the inventive method used to form the magnetotherapeutic back massager relies upon generally magnetically-inert materials so that the magnetic fields present about the magnets used in the magnetotherapeutic back massager are not unduly limited or diminished. As shown in FIG. 1, a roller blank generally serves as a core for the magnetotherapeutic back massager constructed as a result of the present inventive method.

In FIG. 1, the roller blank 20 is preferably made of latex rubber or the like, but can be constructed of like materials that serve the back massaging purposes of the present invention. The roller blank 20 has a central cylindrical core 22 having open ends 24, 26 that lead into the hollow cavity defined by the cylindrical core 22. Circumscribing the cylindrical core 22, and adjacent but spaced apart from the open ends 24, 26, are two cylindrical projections 30, 32 which articulate circumferentially about the cylindrical core 22 perpendicular to the longitudinal axis of the cylindrical core 22. The cylindrical projections 30, 32 provide housing or seats for the magnets providing the magnetotherapeutic portion of the resulting back massager.

The cylindrical core is approximately four to six inches (4–6") in length with the cylindrical projections 30, 32 offset from the open ends 24, 26 by approximately one inch (1"). The circular projections 30, 32 project away from the cylindrical core 22 approximately one inch and are approximately half an inch wide. The two circular projections 30, 32 may be separated by a space of approximately three to five inches (3–5") so that the resulting bi-lobed magnetotherapeutic back massager has the lobes centrally located over each of the circular projections 30, 32.

As shown in FIG. 1, the circular projections 30, 32 have indentations, or holes, 40. Each of these indentations serve to receive one of the circular magnets during the manufacturing procedure set forth herein. The magnet indentations may be separated by a slight space or may otherwise accommodate magnets of a circular or other shape in a manner by which such magnets may be easily received and associated with the circular projections 30, 32.

In an alternative embodiment, the roller blank 20 has circular projections 30, 32 which have a groove or furrow 44 about their perimeter. Magnets can be fitted into this groove 44 in a manner similar to that set forth below for the magnet indentations 40 (FIG. 1).

Having constructed a roller blank to serve as a core for the magnetotherapeutic back massager, the permanent magnets by which magnetic fields can be imparted by the resulting magnetotherapeutic back massager are then associated with the roller blank 20.

Figure 3:
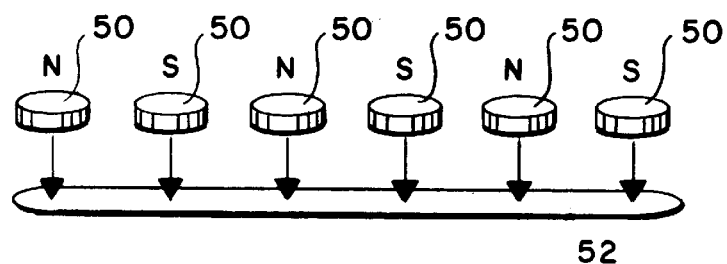
FIG. 3 is a front elevational view of the magnet-supporting strip with magnets to be supported by the magnet-supporting strip as used in the present inventive method.

FIG. 3 shows a number of magnets 50 in association with a magnets-supporting strip 52. The magnet-supporting strip 52 may support the magnets 50 by adhesion, magnetism, or otherwise. If the magnets 50 are supported by adhesion by the magnet-supporting strip 52, then the adhesive attachment between the magnets 50 and the magnet-supporting strip 52 should be of a temporary nature so that the magnet-supporting strip can be easily separated from the magnets 50, yet securely retaining the magnets 50 while they are to be associated with the magnet-supporting strip.

Preferably, the magnet-supporting strip 52 is made of a ferromagnetic material such as steel or iron and is of a sufficiently thin nature so that it is flexible. The flexible nature of the magnet-supporting strip 52 allows it to conform to the circular circumference of the circular projections 30, 32 during the application of the magnets 50 to the circular projections 30, 32.

The magnets 50 are generally strong in nature generating strong magnetic fields. The magnets 50 may be such as are known as Alnico magnets. Alternatively, magnets of lesser magnet strength can be used to good effect in the present invention. As shown in FIG. 3, the magnets are disposed so that the faces opposite the magnetic strip 52 alternate in polarity. As shown in FIG. 3, the alternation takes place (from left to right) by alternating north and south poles.

The magnet-supporting strip 52 is approximately 4"in length and generally corresponds to approximately one-half the circumference of the circular projections 30, 32. In this way, half of the magnets 50 required by the circular projections 30, 32 may be applied to the circular projections during the process step where the magnets 50 are associated with the roller blank 20 and the circular projections 30, 32.

The magnets 50 may be arranged upon the magnet-supporting strip 52 by machine, hand, or otherwise and should be ready for association with the roller blank 20 prior to the assembly process.

Having provided the roller blank 20 with its circular projections 30, 32, as well as the magnet-supporting strip 52 with its magnets 50, the magnets 50 are then ready for association with the roller blank. Generally, four magnet-supporting strips are used in order to supply the circular projections 30, 32 with sufficient magnets to fill up the magnet indentations 40. In an alternative embodiment, a magnetic strip may be of a length the same as the circumference of a circular projection 30, 32 so that one magnet-supporting strip 52 when filled to capacity with magnets, could then also provide the circular projections 31), 32 with all the magnets the circular projection requires.

The roller blank 20 and magnet-supporting strip 52 with magnets 50 are ready, the magnet-supporting strip 52 with its magnets 50 is then applied to one of the circular projections 30. The side of the magnets 50 opposite the magnet-supporting strip 52 is inserted into the magnet indentations 40 with one magnet 50 fitting into a corresponding magnet indentation 40. As the magnets 50 are inserted into the magnet indentations 40, the magnet-supporting strip 52 bends or arcs around the circumference of the circular projection 30. After the last magnet 50 is inserted into its corresponding magnet indentation 40, the magnet-supporting strip 52 generally conforms to the corresponding portion of the circular projection circumference. This flexible nature of the magnet-supporting strip allows easy association with the magnets 50 with the roller blank 20. In this way, magnetic fields can be supplied by the resulting magnetotherapeutic back massager.

Once all of the magnets 50 of the magnet-supporting strip 52 have been inserted into the corresponding magnet indentations 40, the magnet-supporting strip 52 is removed from the magnets 50 to leave the magnets 50 in the magnet indentations 40 of the circular projection 30 upon removal of the magnet-supporting strip. The magnets 50 may be sealed in the magnet indentations 40 by adding additional latex material similar to that used in forming the roller blank, or other material as appropriate. This attachment process may take place prior to or after the removal of the magnet-supporting strip 52 so long as the magnet-supporting strip 52 can then be removed from the roller blank 20. The association of the magnets 50 with the magnet indentations 40 or groove 44 then continues until all available space provided by the circular projections 30, 32 are filled with magnets or magnetic field providing devices or items.

Upon so associating the magnets 50 with the roller blank 20 and its circular projections 30, 32, the roller blank is made magnetic and the process has been facilitated by the use of the magnet-supporting strip. It should be noted that the use of latex rubber for the construction of the roller blank 20 provides an inexpensive and durable material that does not interfere with the magnetic properties of the magnets 50. This is unlike metals which may exhibit ferromagnetic, diamagnetic, and/or paramagnetic properties that might interfere with or diminish the magnetic properties of the resulting magnetotherapeutic back massager.

Figure 4:
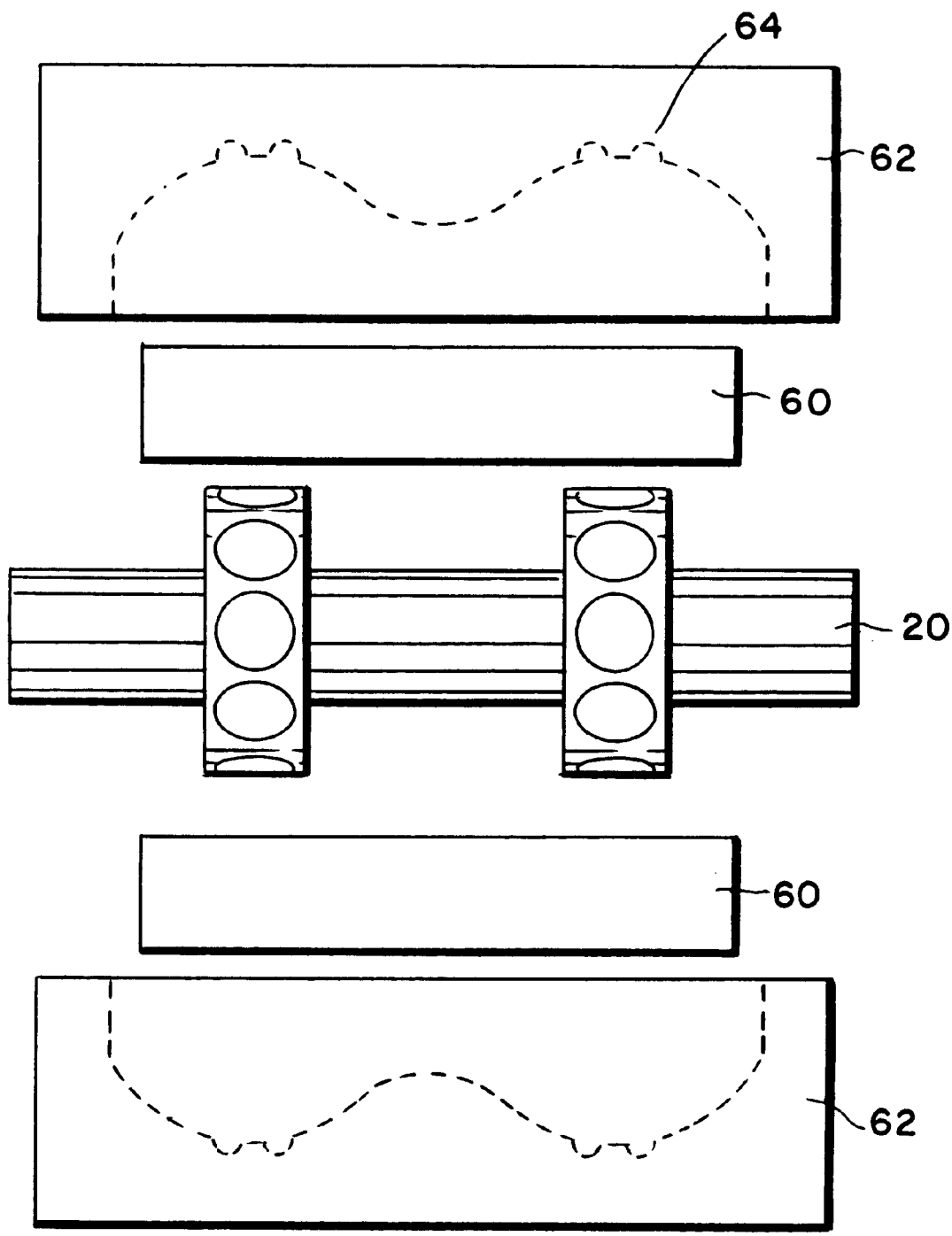
FIG. 4 shows a front elevational view of a completed magnetic roller core about to be fitted with a cover during the molding process.
Figure 5:
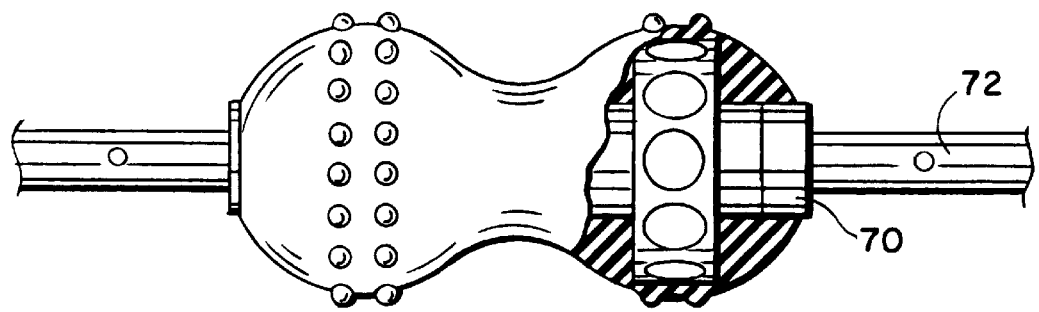
FIG. 5 shows a front elevational view of a completed magnetotherapeutic roller as constructed according to the method of the present invention.
Figure 6:
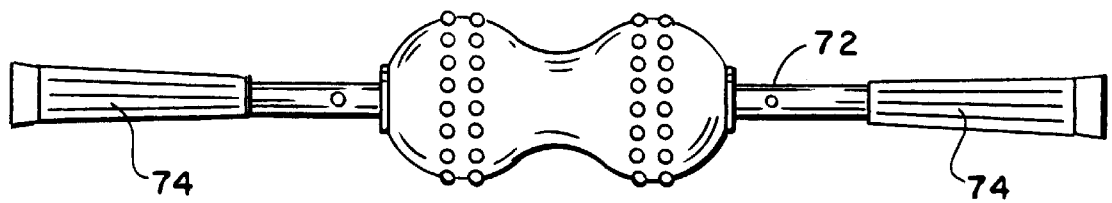
FIG. 6 shows a front view of a completed magnetotherapeutic roller.

Upon so forming the magnetic roller blank via the process set forth above, the remaining portions of the magnetotherapeutic back massager may be constructed along the lines currently known in the art. As shown in FIG. 4, once the roller blank 20 has been fitted with its magnets 50 via the magnet-supporting strip 52, cover material in the form of is blanks or the like 60 may be formed or pressed over the magnetized roller blank 20 by use of molds 62 or the like. The molds 62 may provide for the formation of knobs or stubs 64 which can serve to provide a cover that has means by which the pressure applied by the massager can be concentrated into certain areas during the rolling of the magnetotherapeutic back massager over the back or other body portion of the person being massaged. Additionally, and as shown in FIG. 5, bearings 70 can be added at both ends of the roller blank 20, namely at the open ends 24, 26. The bearings 70 provide means by which the formed roller core can articulate rotatably with respect to a central spindle shaft 72. As shown in FIG. 6, the central spindle shaft 72 may have handles 74 attached at opposite ends so as to make grasping and manipulating the magnetotherapeutic back massager easier.

While the present invention has been described with regards to particular embodiments, it is recognized that additional variations of the present invention may be devised without departing from the inventive concept.

What I claim is:

1. A method for making a magnetotherapeutic back massager, comprising:
   providing a roller blank as a core for the magnetotherapeutic back massager;
   providing a magnet-supporting strip;
   arranging magnets upon said magnet-supporting strip;
   engaging said roller blank with said magnets so as to join said magnets to said roller blank;
   attaching said magnets to said roller blank; and
   disengaging said magnet-supporting strip from said magnets and said roller blank; whereby
   said roller blank is made magnetic by the addition of said magnets in a convenient and expedient manner facilitating manufacture and construction.

2. The method for making a magnetotherapeutic back massager as set forth in claim 1, wherein the step of providing a roller blank further comprises:
   at least one circular projection with which said magnets are associated.

3. The method for making a magnetotherapeutic back massager as set forth in claim 2, wherein the step of providing a roller blank further comprises:
   providing a roller blank having a central, hollow cylinder about which are disposed two circular projections for holding magnets, said two circular projections in parallel, spaced apart relation.

4. The method for making a magnetotherapeutic back massager as set forth in claim 3, wherein the step of providing a roller blank further comprises:
   providing a latex roller blank.

5. The method for making a magnetotherapeutic back massager as set forth in claim 1, wherein the step of providing a magnet-supporting strip further comprises:
   providing a magnet-supporting strip of length approximately one-half (½) the circumference of said roller blank engaging said magnets.

6. The method for making a magnetotherapeutic back massager as set forth in claim 1, wherein the step of providing a magnet-supporting strip further comprises:
   providing a magnetizable strip that supports said magnets by magnetic attraction.

7. The method for making a magnetotherapeutic back massager as set forth in claim 6, wherein the step of providing a magnet-supporting strip further comprises:
   a ferromagnetic strip.

8. The method for making a magnetotherapeutic back massager as set forth in claim 1, wherein the step of arranging magnets upon said magnet-supporting strip further comprises:
   providing a series of magnets for incorporation into said roller blank.

9. The method for making a magnetotherapeutic back massager as set forth in claim 8, wherein the step of providing a series of magnets for incorporation into said roller blank further comprises:
   providing a series of circular magnets.

10. The method for making a magnetotherapeutic back massager as set forth in claim 1, wherein the step of arranging magnets upon said magnet-supporting strip further comprises:
    arranging said magnets upon said magnet-supporting strip so that the polarities of said magnets alternate.

11. The method for making a magnetotherapeutic back massager as set forth in claim 1, wherein the step of engaging said roller blank with said magnets further comprises:
    fitting said magnets against said roller blank so that said magnet-supporting strip faces outward and a side of said magnets opposite said magnet-supporting strip engages said roller blank.

12. The method for making a magnetotherapeutic back massager as set forth in claim 1, wherein the step of attaching said magnets to said roller blank further comprises:
    adding additional material about said magnets to secure them to said roller blank, said material being the same as material used in said roller blank.

13. The method for making a magnetotherapeutic back massager as set forth in claim 1, further comprising:
    providing a roller bearing, said roller bearing attached to said roller blank.

14. The method for making a magnetotherapeutic back massager as set forth in claim 1, further comprising:
    providing a cover, said cover attached to and covering said roller blank.

15. The method for making a magnetotherapeutic back massager as set forth in claim 14 wherein the step of providing a cover, further comprises:
    providing a knobbed cover.

16. The method for making a magnetotherapeutic back massager as set forth in claim 1, further comprising:
    providing a spindle shaft, said spindle shaft coupled to said roller blank.

17. The method for making a magnetotherapeutic back massager as set forth in claim 16, wherein the step of providing a spindle shaft further comprises:
    providing a pair of handles, one at each end of said spindle shaft.

18. A method for making a magnetotherapeutic back massage, comprising:
    providing a latex roller blank as a core for the magnetotherapeutic back massager, said roller blank having a central, hollow cylinder about which are disposed two circular projections for holding magnets, said two circular projections in parallel, spaced apart relation;
    providing a ferromagnetic magnet-supporting strip that supports magnets by magnetic attraction, said magnet-supporting strip of length approximately one-half (½) the circumference of one of said circular projections;
    providing a series of circular magnets for incorporation into said roller blank;
    arranging magnets upon said magnet-supporting strip;
    engaging said roller blank with said magnets so as to join said magnets to said roller blank;
    attaching said magnets to said roller blank;
    disengaging said magnet-supporting strip from said magnets and said roller blank;
    providing a roller bearing, said roller bearing attached to said roller blank;
    providing a knobbed cover, said knobbed cover attached to and covering said roller blank; and
    providing a spindle shaft, said spindle shaft having a pair of handles, one at each end of said spindle shaft, said spindle shaft coupled to said roller blank; whereby said roller blank is made magnetic by the addition of said magnets in a convenient and expedient manner facilitating manufacture and construction, and a magnetotherapeutic back massager is provided.

19. The method for making a magnetotherapeutic back massager as set forth in claim 1, wherein the step of arranging magnets upon said magnet-supporting strip further comprises:

arranging said magnets upon said magnet-supporting strip so that the polarities of said magnets alternate.

20. The method for making a magnetotherapeutic back massager as set forth in claim 1, wherein the step of engaging said roller blank with said magnets further comprises:

fitting said magnets against said roller blank so that said magnet-supporting strip faces outward and a side of said magnets opposite said magnet-supporting strip engages said roller blank.

21. The method for making a magnetotherapeutic back massager as set forth in claim 1, wherein the step of attaching said magnets to said roller blank further comprises:

adding additional material about said magnets to secure them to said roller blank, said material being the same as material used in said roller blank.

22. A method for making a magnetotherapeutic back massager, comprising:

providing a latex roller blank as a core for the magnetotherapeutic back massager, said roller blank having a central, hollow cylinder about which are disposed two circular projections for holding magnets, said two circular projections in parallel, spaced apart relation;

providing a ferromagnetic magnet-supporting strip that supports magnets by magnetic attraction, said magnet-supporting strip of length approximately one-half (½) the circumference of one of said circular projections;

providing a series of circular magnets for incorporation into said roller blank;

arranging magnets upon said magnet-supporting strip so that the polarities of said magnets alternate;

engaging said roller blank with said magnets so as to join said magnets to said roller blank by fitting said magnets against said roller blank so that said magnet-supporting strip faces outward and a side of said magnets opposite said magnet-supporting strip engages said roller blank;

attaching said magnets to said roller blank by adding additional material about said magnets to secure them to said roller blank, said material being the same as material used in said roller blank;

disengaging said magnet-supporting strip from said magnets and said roller blank;

providing a roller bearing, said roller bearing attached to said roller blank;

providing a knobbed cover, said knobbed cover attached to and covering said roller blank; and providing a spindle shaft, said spindle shaft having a pair of handles, one at each end of said spindle shaft, said spindle shaft coupled to said roller blank; whereby said roller blank is made magnetic by the addition of said magnets in a convenient and expedient manner facilitating manufacture and construction, and a magnetotherapeutic back massager is provided.

* * * * *